(12) United States Patent
Kurfirst

(10) Patent No.: US 11,742,086 B2
(45) Date of Patent: Aug. 29, 2023

(54) SYSTEMS AND METHODS FOR DETERMINING AND USING HEALTH CONDITIONS BASED ON MACHINE LEARNING ALGORITHMS AND A SMART VITAL DEVICE

(71) Applicant: Aetna Inc., Hartford, CT (US)

(72) Inventor: Dwayne Kurfirst, Hartford, CT (US)

(73) Assignee: Aetna Inc., Hartford, CT (US)

( * ) Notice: Subject to any disclaimer, the term of this patent is extended or adjusted under 35 U.S.C. 154(b) by 565 days.

(21) Appl. No.: 16/886,464

(22) Filed: May 28, 2020

(65) Prior Publication Data

US 2021/0375456 A1 Dec. 2, 2021

(51) Int. Cl.
*G16H 50/20* (2018.01)
*G16H 50/30* (2018.01)
*G06N 5/04* (2023.01)
*G06N 20/00* (2019.01)

(52) U.S. Cl.
CPC .............. *G16H 50/20* (2018.01); *G06N 5/04* (2013.01); *G06N 20/00* (2019.01); *G16H 50/30* (2018.01)

(58) Field of Classification Search
CPC .......... G16H 50/20; G16H 50/30; G06N 5/04; G06N 20/00
See application file for complete search history.

(56) References Cited

U.S. PATENT DOCUMENTS

| | | | |
|---|---|---|---|
| 9,858,388 B1 * | 1/2018 | Ashoori | G16H 50/70 |
| 2018/0090229 A1 * | 3/2018 | Sanyal | H04L 67/125 |
| 2018/0144614 A1 * | 5/2018 | Knechtel | G08B 27/006 |
| 2020/0202996 A1 * | 6/2020 | Rastogi | G16H 20/40 |
| 2020/0245873 A1 * | 8/2020 | Frank | A61B 5/0823 |
| 2020/0303047 A1 * | 9/2020 | Bostic | G16H 50/50 |
| 2021/0030276 A1 * | 2/2021 | Li | A61B 5/4803 |
| 2021/0059616 A1 * | 3/2021 | Abrol | A61B 5/0022 |
| 2021/0074436 A1 * | 3/2021 | Trim | A47L 9/2852 |

FOREIGN PATENT DOCUMENTS

WO WO-2018172352 A1 * 9/2018 ............... A61B 5/01

* cited by examiner

*Primary Examiner* — Roberto Borja
(74) *Attorney, Agent, or Firm* — Leydig, Voit & Mayer, Ltd.

(57) ABSTRACT

In some instances, the disclosure provides a method performed by a smart vital device. The method comprises receiving sensor information indicating one or more health characteristics associated with an individual, wherein the sensor information comprises audio information indicating audio signals from a surrounding environment and temperature information indicating temperature readings from the surrounding environment, determining one or more health audio characteristics of the individual based on inputting the audio signals into one or more health condition machine learning datasets, determining one or more health temperature characteristics of the individual based on the temperature readings from the surrounding environment, determining one or more health conditions of the individual based on the one or more health audio characteristics and the one or more health temperature characteristics, and outputting the one or more health conditions of the individual.

20 Claims, 8 Drawing Sheets

200

500

SYSTEMS AND METHODS FOR DETERMINING AND USING HEALTH CONDITIONS BASED ON MACHINE LEARNING ALGORITHMS AND A SMART VITAL DEVICE

BACKGROUND

The impact of viruses and other diseases is significant even during a typical flu season and the prevention of another global pandemic is a desire shared by many enterprise organizations. Even in a global pandemic, some enterprise organizations have physical storefronts and retail stores that need to remain open. For instance, individuals may require necessities such as food or medication regardless of the situation. Further, these individuals might not even realize they are sick and by visiting these stores, may inadvertently spread diseases to other individuals or employees. Because of the current pandemic, enterprise organizations with physical storefronts and retail stores have implemented many solutions in an attempt to curb the spread of these diseases. However, many of these solutions are not automated and might not be as effective at widespread prevention. For instance, even if employees were able to notice an individual displayed health symptoms, which would be extremely difficult considering the employee has other priorities, the employee would still have to interact with that individual, which may cause the disease to spread to the employee. Accordingly, there remains a technical need for monitoring symptoms of individuals within a storefront and for alerting individuals of their symptoms in an attempt to prevent the spread of diseases.

SUMMARY

In some instances, the disclosure a system comprising a first smart vital device and an enterprise computing system. The first smart vital device comprises one or more first processors and a first non-transitory computer-readable medium having first processor-executable instructions stored thereon. The first processor-executable instructions, when executed, facilitate obtaining sensor information indicating one or more health characteristics associated with an individual, determining one or more health conditions of the individual based on inputting the sensor information into one or more health condition machine learning datasets, outputting one or more notifications indicating the one or more health conditions of the individual, and providing, to an enterprise computing system, the one or more health conditions of the individual. The enterprise computing system comprises one or more second processors and a second non-transitory computer-readable medium having second processor-executable instructions stored thereon. The second processor-executable instructions, when executed, facilitate aggregating a plurality of health conditions from a plurality of smart vital devices, wherein the plurality of smart vital devices comprises the first smart vital device, determining one or more health trends based on inputting the plurality of health conditions from the plurality of smart vital devices into one or more health trend machine learning datasets, updating the one or more health trend machine learning datasets based on the one or more health trends, and outputting information indicating the one or more health trends.

In other instances, the disclosure provides a method performed by a smart vital device. The method comprises receiving, by a smart vital device, sensor information indicating one or more health characteristics associated with an individual, wherein the sensor information comprises audio information indicating audio signals from a surrounding environment and temperature information indicating temperature readings from the surrounding environment, determining, by the smart vital device, one or more health audio characteristics of the individual based on inputting the audio signals into one or more health condition machine learning datasets, determining, by the smart vital device, one or more health temperature characteristics of the individual based on the temperature readings from the surrounding environment, determining, by the smart vital device, one or more health conditions of the individual based on the one or more health audio characteristics and the one or more health temperature characteristics, and outputting, by the smart vital device, the one or more health conditions of the individual.

In yet other instances, the disclosure provides a non-transitory computer-readable medium having processor-executable instructions stored thereon. The processor-executable instructions, when executed, facilitate receiving sensor information indicating one or more health characteristics associated with an individual, wherein the sensor information comprises audio information indicating audio signals from a surrounding environment and temperature information indicating temperature readings from the surrounding environment, determining one or more health audio characteristics of the individual based on inputting the audio signals into one or more health condition machine learning datasets, determining one or more health temperature characteristics of the individual based on the temperature readings from the surrounding environment, determining one or more health conditions of the individual based on the one or more health audio characteristics and the one or more health temperature characteristics, and outputting the one or more health conditions of the individual.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Embodiments of the presented invention will now be described more fully hereinafter with reference to the accompanying FIGS., in which some, but not all, embodiments of the invention are shown. Indeed, the invention may be embodied in any different forms and should not be construed as limited to the embodiments set forth herein; rather, these embodiments are provided so that the disclosure will satisfy applicable legal requirements. Where possible, any terms expressed in the singular form herein are meant to also include the plural form and vice versa, unless explicitly stated otherwise. Also, as used herein, the term "a" and/or "an" shall mean "one or more" even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on".

Figure 1:
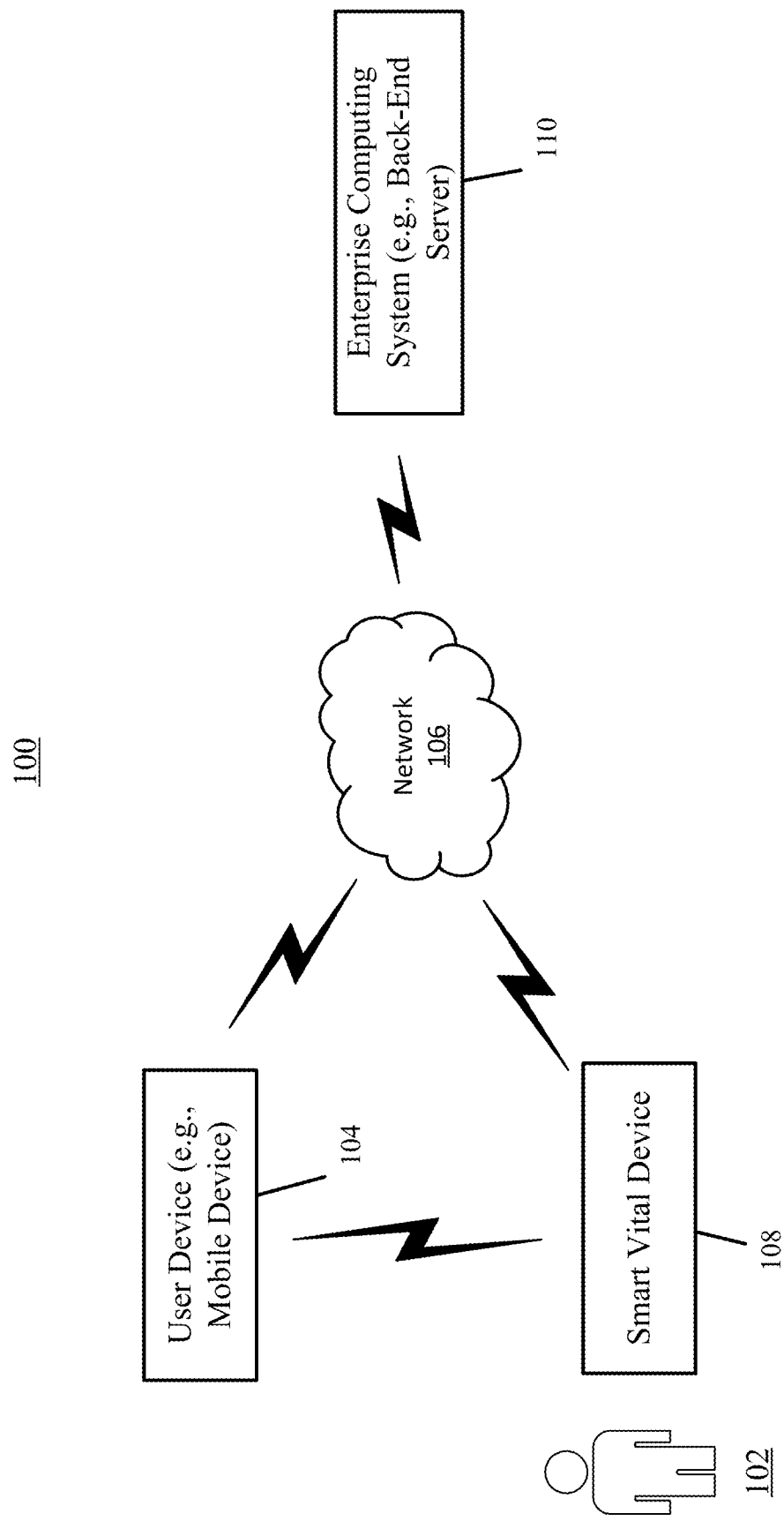
FIG. 1 is a simplified block diagram depicting an exemplary computing environment in accordance with one or more exemplary embodiments of the present application.

Systems, methods, and computer program products are herein disclosed that provide for determining and using health conditions based on machine learning algorithms and a smart vital device. FIG. 1 is a simplified block diagram depicting an exemplary environment in accordance with an exemplary embodiment of the present application. The environment 100 includes an individual (e.g., user) 102, a user device (e.g., mobile devices) 104 associated with the individual 102, a smart vital device 108, and an enterprise computing system (e.g., back-end server) 110. Although the entities within environment 100 may be described below and/or depicted in the FIGS. as being singular entities, it will be appreciated that the entities and functionalities discussed herein may be implemented by and/or include one or more entities. For instance, the smart vital device 108 may be a singular smart vital device 108 located in a physical location such as a storefront or may be multiple smart vital devices 108 located within the physical location or spread across multiple locations.

The entities within the environment 100 such as the user device 104, the smart vital device 108, and/or the enterprise computing system 110 may be operatively coupled to (e.g., in communication with) other systems within the environment 100 via the network 106. The network 106 may be a global area network (GAN) such as the Internet, a wide area network (WAN), a local area network (LAN), or any other type of network or combination of networks. The network 106 may provide a wireline, wireless, or a combination of wireline and wireless communication between the entities within the environment 100.

Individual 102 may be associated with and/or operate a user device 104. For instance, the user device 104 may be a mobile phone such as a smartphone that is owned by the individual 102. The individual 102 may provide information to the other entities of environment 100 such as the enterprise computing system 110 and/or the smart vital device 108 using the user device 104. For example, the user device 104 may receive user input from the individual 102 such as indications to download and/or operate a software application associated with an enterprise organization. The enterprise organization may be any type of corporation, company, organization, and/or other institution.

The user device 104 may be and/or include, but is not limited to, a desktop, laptop, tablet, mobile device (e.g., smartphone device, or other mobile device), smart watch, an internet of things (IOT) device, or any other type of computing device that generally comprises one or more communication components, one or more processing components, and one or more memory components. The user device 104 may be able to execute software applications managed by, in communication with, and/or otherwise associated with the enterprise organization.

The smart vital device 108 determines health conditions (e.g., symptoms) and/or medical conditions (e.g., whether the user is sick) of the individual 102. The smart vital device 108 provides this information indicating the health conditions and/or medical conditions to the user device 104 and/or the enterprise computing system 110. The smart vital device 108 may be located and/or installed within a physical location associated with the enterprise organization. For example, the enterprise organization may own and/or operate physical locations (e.g., storefronts, dwellings, places, settings, stands, and so on) and use these physical locations to provide goods and/or services to individuals. In some examples, the enterprise organization is a pharmacy operation such as a pharmacy chain and may provide individuals with a location to pick-up their medications as well as groceries/other food products and pharmacy supplies. The enterprise organization may own and/or manage numerous physical locations such as physical storefronts and these locations may provide medications (e.g., prescriptions), groceries/other food products, and pharmacy supplies to many individuals including individual 102. The smart vital device 108 may be located and/or installed within these storefronts. For instance, the smart vital device 108 may installed in entryways of the physical location (e.g., storefront) and/or in other locations such as within the aisles, at the check-out locations (e.g., automated and/or employee operated locations), and/or by a pharmacy area. In some variations, the smart vital device 108 may be installed on top of several mirrors and/or may be located substantially eye-level of individuals visiting the physical location.

The smart vital device 108 may use one or more sensors to detect and/or determine health conditions (e.g., symptoms) of the individual 102 such as visitors of the physical location owned/managed by the enterprise organization. For example, the smart vital device 108 may include one or more sensors including, but not limited to, one or more temperature sensors and/or audio sensors. The sensors may receive information from the individual 102 such as information indicating a temperature of the individual 102 and/or audio signals. The smart vital device 108 may use machine learning algorithms (e.g., supervised artificial intelligence algorithms, unsupervised artificial intelligence algorithms, and/or deep learning algorithms) to determine whether the sensor information indicates the individual 102 has one or more health conditions such as whether the individual 102 has a fever or elevated temperature indicative of being sick and/or whether the individual 102 coughed, sneezed, and/or other audio cues indicative of the individual 102 being sick.

Based on the determined health condition, the smart vital device 108 provides an indication or other type of notification/alert to the individual 102 of their symptoms and/or provides instructions for the individual 102. For example, the smart vital device 108 may include an output device such as a microphone or other audio output device that outputs a notification indicating the health condition and/or medical condition (e.g., the individual 102 may be sick). For instance, the individual 102 may have a low-grade fever that he or she is not aware of and the smart vital device 108 may alert the individual of this. The alert may further indicate steps to prevent the spread of a disease/affliction and/or mitigation tactics such as providing a medicine aisle to the individual. The smart vital device 108 may also provide the determined health conditions to the enterprise computing system 110 such as a back-end server. The smart vital device 108 will be described in further detail below.

The enterprise computing system 110 is a computing system that is associated with the enterprise organization. The enterprise computing system 110 includes one or more computing devices, computing platforms, systems, servers, and/or other apparatuses capable of performing tasks, functions, and/or other actions for the enterprise organization. In some instances, the enterprise computing system 110 may, for example, receive information from the smart vital device 108 and/or the user device 104. For instance, the enterprise computing system 110 may receive information indicating the one or more health conditions from the smart vital device 108.

The enterprise computing system 110 determines one or more trends based on the one or more health conditions and using machine learning algorithms (e.g., supervised artificial intelligence algorithms, unsupervised artificial intelligence algorithms, and/or deep learning algorithms) The machine learning algorithm used by the enterprise computing system 110 to determine the trends may be different from the machine learning algorithm used by the smart vital device 108. The enterprise computing system 110 may receive health conditions from multiple different smart vital device 108. In some instances, the multiple different smart vital devices 108 may be located in different geographical areas and the enterprise computing system 110 may further receive information indicating a geographical location and date/time associated with the health condition.

The enterprise computing system 110 may input the information from the smart vital devices 108, including the health conditions, date/time stamp, and/or geographical location, into the machine learning algorithms to generate the trends. The enterprise computing system 110 may determine information from the trends such as a peak of an infection and/or device.

Additionally, and/or alternatively, the enterprise computing system 110 may determine recommendations based on the trend information (e.g., peaks). The enterprise computing system 110 may provide the trends and/or recommendations to another computing device such as a computing device at a physical storefront and/or another computing device associated with the enterprise organization. For instance, based on the trend information, the enterprise computing system 110 may determine a particular geographical area may be suffering from an affliction and a date that the affliction will peak. Based on this determination, the enterprise computing system 110 may provide a recommendation for the physical storefronts of the enterprise organization to store up on essentials for the affliction such as additional tissue paper, medication, and/or other types of products that assist individuals suffering from the affliction. The enterprise computing system 110 will be described in further detail below.

The enterprise computing system 110 may be implemented using one or more computing platforms, devices, servers, and/or otherwise apparatuses that are capable of using machine learning algorithms to determine trends. In some variations, the enterprise computing system 110 may be implemented as engines, software functions, and/or applications. In other words, the functionalities of the enterprise computing system 110 and/or the enterprise computing system 110 may be implemented as software instructions stored in a storage (e.g., memory) and executed by one or more processors.

It will be appreciated that the exemplary environment depicted in FIG. 1 is merely an example, and that the principles discussed herein may also be applicable to other situations—for example, including other types of institutions, organizations, devices, systems, and network configurations. As will be described herein, the environment 100 may be used by health care enterprise organizations. However, in some variations, the environment 100 and the flowcharts, processes, event sequences, and/or other descriptions below may be used for other industries such as finance, manufacturing, and/or other services.

Figure 2:
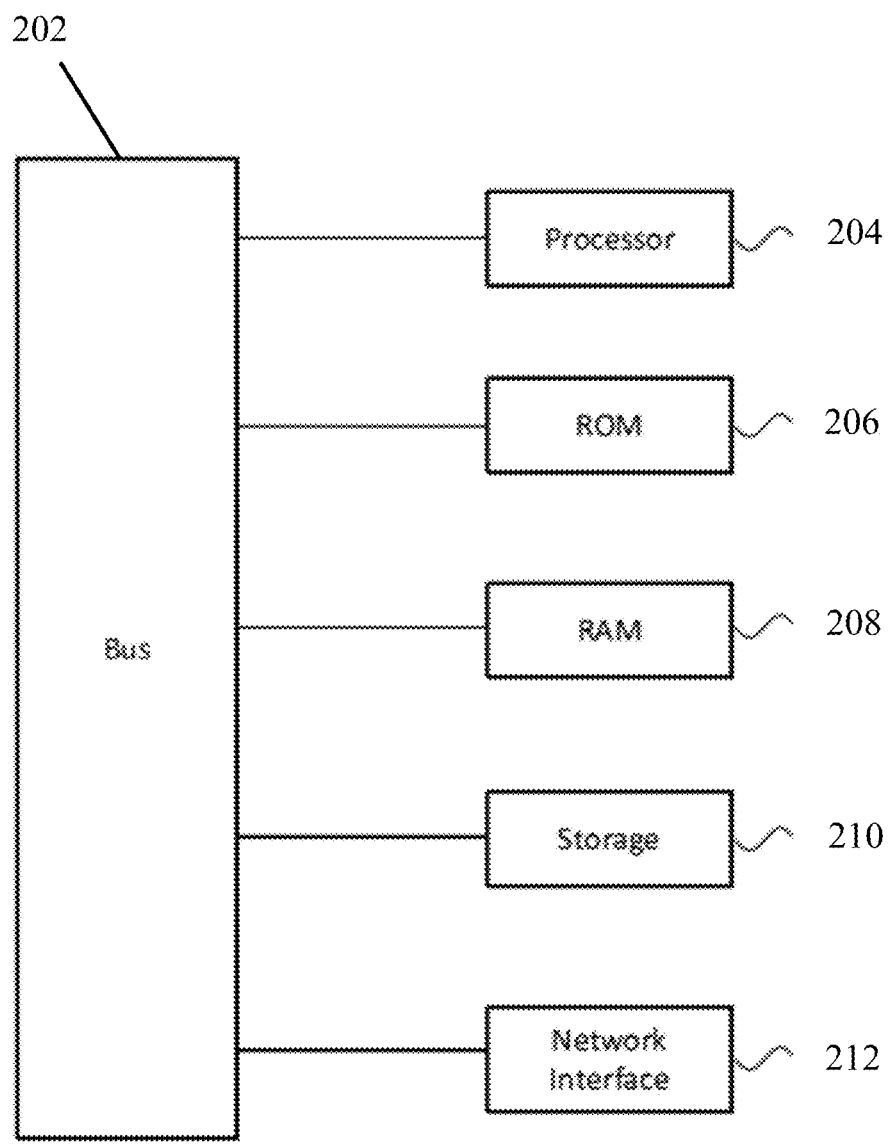
FIG. 2 is a simplified block diagram of one or more devices or systems within the exemplary environment of FIG. 1.

FIG. 2 is a block diagram of an exemplary system and/or device 200 within the environment 100. The device/system 200 includes a processor 204, such as a central processing unit (CPU), controller, and/or logic, that executes computer executable instructions for performing the functions, processes, and/or methods described herein. In some examples, the computer executable instructions are locally stored and accessed from a non-transitory computer readable medium, such as storage 210, which may be a hard drive or flash drive. Read Only Memory (ROM) 206 includes computer executable instructions for initializing the processor 204, while the random-access memory (RAM) 208 is the main memory for loading and processing instructions executed by the processor 204. The network interface 212 may connect to a wired network or cellular network and to a local area network or wide area network, such as the network 106. The device/system 200 may also include a bus 202 that connects the processor 204, ROM 206, RAM 208, storage 210, and/or the network interface 212. The components within the device/system 200 may use the bus 202 to communicate with each other. The components within the device/system 200 is merely exemplary and might not be inclusive of every component, device, computing platform, and/or computing apparatus within the device/system 200. For example, as will be described below, the smart vital device 108 may include some of the components within the device/system 200 and may also include further components such as one or more sensors. Additionally, and/or alternatively, the device/system 200 may further include components that might not be included within the entities within environment 100.

Figure 3:
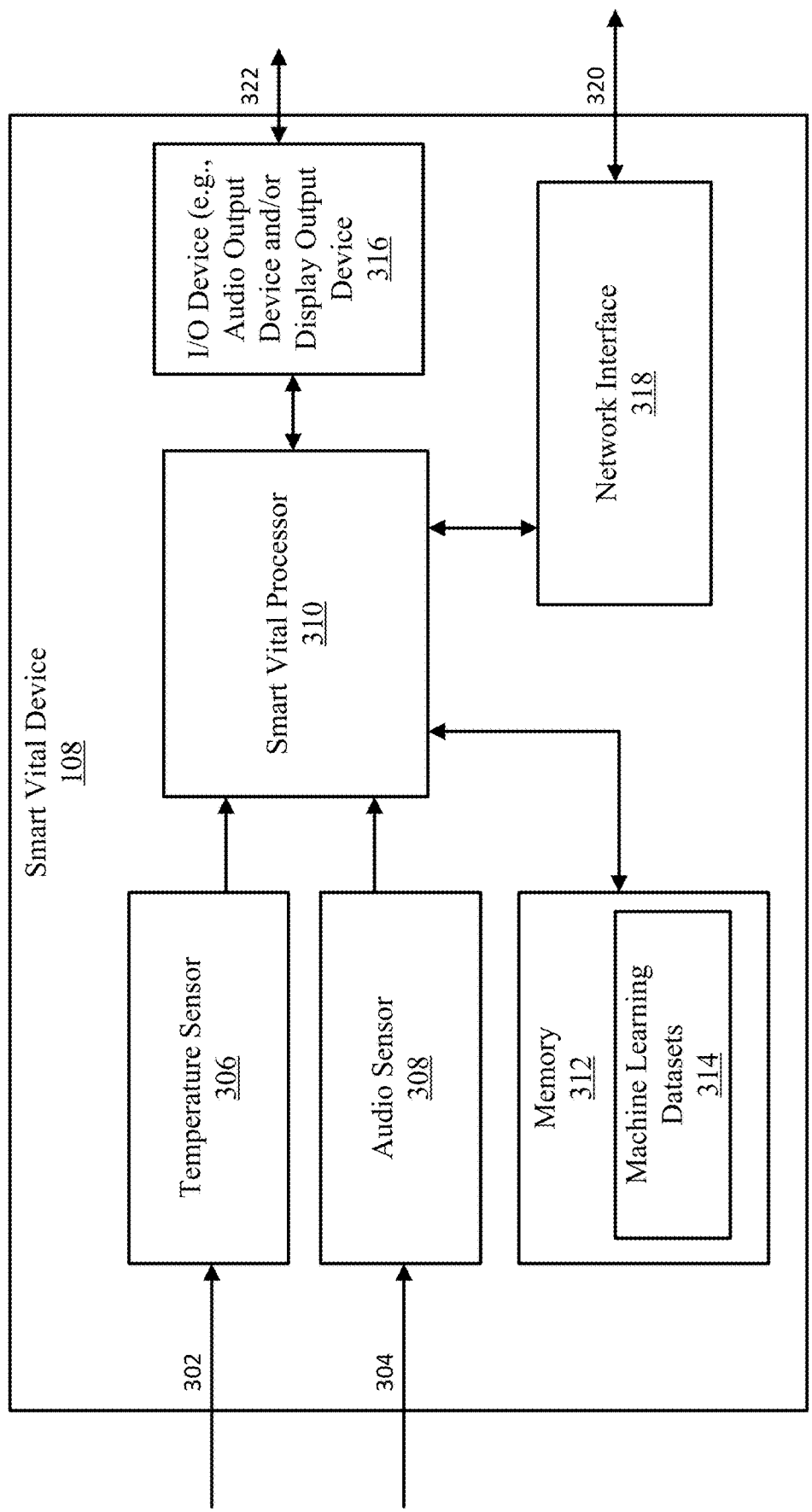
FIG. 3 is another simplified block diagram depicting a smart vital device in accordance with one or more exemplary embodiments of the present application.

FIG. 3 is a simplified block diagram depicting a smart vital device 108 in accordance with one or more exemplary embodiments of the present application. For example, the smart vital device 108 includes one or more sensors including, but not limited to, the temperature sensor 306 and the audio sensor 308. The temperature sensor 306 receives information 302 indicating temperatures of an area surrounding the smart vital device 108. These temperatures may include a temperature of an individual (e.g., individual 102) within the vicinity of the smart vital device 108. The temperature sensor 306 may be any type of sensor that is capable of detecting temperatures of the surrounding environment and may be/include one or more infrared (IR) temperature sensors, thermistors, thermal cameras, and/or resistance temperature detectors (RTDs). For instance, the temperature sensor 306 may detect temperature information that includes temperature(s) associated with the individual 102 and provide the temperature information to the smart vital processor 310.

The audio sensor 308 receives audio information 304 from the area surrounding the smart vital device 108. For example, the audio sensor 308 may be any type of device that detects and/or monitors audio signals/sounds from the area surrounding the device 108. For instance, the audio sensor 308 may be and/or include a microphone and/or other types of audio devices that may convert sounds into electrical signals (i.e., audio signals). The audio sensor 308 may provide the audio signals/sounds to the processor 310. In some instances, the audio signals may be used to detect health conditions of the individual 102 such as coughs, sneezes, and/or other indications the individual 102 may be sick.

While only the temperature sensor 306 and the audio sensor 308 are shown in FIG. 3, in some examples, the smart vital device 108 may include additional sensors such as a humidity sensor and/or a visual sensor (e.g., camera). For example, the humidity sensor may detect and measure water vapor including the humidity/moisture of the area surrounding the smart vital device 108. For instance, when an individual 102 passes by the smart vital device 108, the humidity sensor may detect information indicating the humidity/moisture of the individual 102 and provide it to the smart vital processor 310. The smart vital processor 310 may use this information to determine whether the individual 102 is sweating and/or perspiring (e.g., whether the individual 102 may have a cold sweat or other health condition).

The visual sensor (e.g., a camera, vision system, and/or other type of sensor that is capable of capturing images of the individual 102) may capture an image and/or video of the individual 102. For example, when the individual 102 passes by the smart vital device 108 (e.g., using motion detection and/or other methods of detecting user movement), the visual sensor may capture an image and provide the image to the smart vital processor 310. The smart vital processor 310 may use the image to determine whether the individual 102 is sweating, limping, walking slowly, holding onto the side of a structure indicting they may be dizzy, feint, and/or weak. The smart vital processor 310 may further determine whether the individual 102 has eye dilation, skin discoloration, and/or pimples, which may potentially indicate chicken pox, measles, or other types of contagious skin irritations.

The smart vital processor 310 may be any type of hardware and/or software logic, such as a central processing unit (CPU), RASPBERRY PI processor/logic, controller, and/or logic, that executes computer executable instructions for performing the functions, processes, and/or methods described herein. For example, the smart vital processor 310 receives sensor information from the one or more sensors (e.g., the temperature sensor 306, the audio sensor 308, the humidity sensor, and/or the visual sensor). The smart vital processor 310 retrieves machine learning datasets 314 from memory 312 and uses the machine learning datasets 314 to determine one or more health conditions. For example, the smart vital processor 310 may input the sensor information into the machine learning datasets 314 to determine the health conditions. The machine learning datasets 314 may be an unsupervised machine learning dataset, a supervised machine learning dataset, and/or a deep learning (e.g., neural network) dataset. Furthermore, the health conditions may indicate health characteristics, traits, or symptoms of the individual 102. For example, the health conditions may indicate whether the individual 102 has a fever/elevated temperature, coughs, sneezes, sweating, limping, walking slowly, dizzy, feint, weak, discoloration of the individual's skin color, eye dilation, pimples, and so on.

Additionally, and/or alternatively, in some variations, the smart vital processor 310 may be used to diagnose a disease and/or medical condition. For example, the smart vital processor 310 may use the health conditions associated with the individual 102 to determine a degree of accuracy of a medical condition (e.g., whether the individual 102 is sick). In other words, the smart vital processor 310 may input the sensor information into the machine learning datasets 314 to generate information indicating the health conditions and a degree of accuracy indicating whether the individual 102 is actually sick. For instance, the degree of accuracy may be a percentile such as the individual 102 has a 96% chance of being sick and it is not just a cough, sneeze, or fever.

The smart vital device 308 includes memory 312. The memory 312 includes the machine learning datasets 314 that are used to determine health conditions and/or degree of accuracy as described above and in further detail below. In some examples, the memory 312 may be and/or include a computer-usable or computer-readable medium such as, but not limited to, an electronic, magnetic, optical, electromagnetic, infrared, or semiconductor computer-readable medium. More specific examples (e.g., a non-exhaustive list) of the computer-readable medium may include the following: an electrical connection having one or more wires; a tangible medium such as a portable computer diskette, a hard disk, a time-dependent access memory (RAM such as the RAM 208), a ROM such as ROM 206, an erasable programmable read-only memory (EPROM or Flash memory), a compact disc read-only memory (CD_ROM), or other tangible optical or magnetic storage device. The computer-readable medium may store computer-readable instructions/program code for carrying out operations of embodiments of the present application. For example, when executed by the smart vital processor 310, the computer-readable instructions/program code may carry out operations of the present application including determining health conditions using machine learning.

The smart vital device 108 further includes an input/output (I/O) device 316 such as an audio output device and/or display output device. The I/O device 316 may provide a notification such as an alert to the individual 102 indicating the health condition, the medical condition, and/or the degree of accuracy of the medical condition. For example, the smart vital processor 310 may determine the individual 102 passing by has a health condition such as a fever. The smart vital processor 310 may provide instructions to the I/O device 316 to indicate the health condition to the individual 102 and the I/O device 316 may provide a notification 322 indicating the health condition. The notification 322 may include, but is not limited to, a vocal notification to the individual 102 and/or a displayed notification. For example, the I/O device 316 may include an audio output device and may use a text to speech algorithm to vocalize the alert to the individual 102 such as by vocalizing the health condition (e.g., individual 102 has a fever). Additionally, and/or alternatively, the I/O device 316 may include a display screen that may display a text and/or other types of notification (e.g., lights, LEDS, and so on) to the individual 102 of the health condition.

The smart vital device 108 also includes a network interface 318. The smart vital processor 310 uses the network interface 318 to communicate with other devices and/or systems within the environment 100. The network interface 318 may include the functionalities and/or be the network interface 212 shown in FIG. 2. The smart vital processor 310 may communicate with the enterprise computing system 110 using the network interface 318. For example, the network interface 318 may provide information 320 indicating the health conditions and/or degree of accuracy of the individual 102 to the enterprise computing system 110.

Additionally, and/or alternatively, the network interface 318 may communicate to other devices within the same physical location (e.g., storefront) as the smart vital device 108. For example, the smart vital processor 310 may provide an alert indicating the health condition and/or degree of accuracy of the medical condition to the other device within the storefront. An employee of the storefront may view the alert and provide assistance to the individual 102 such as by informing them of the health condition and directing them to the medicine aisle and so on.

In some examples, by using the smart vital device 108, the individual 102 entering a physical location associated with the enterprise organization may be alerted of a health condition, medical condition, and/or degree of accuracy of the medical condition. The individual 102 might not know of the underlying health condition and based on the alert, may take appropriate action. Furthermore, the employees of the enterprise organization may be aware of the individual's 102 condition and take appropriate action as well. As such, the spread of the affliction may be reduced and/or prevented.

In some variations, the smart vital device 108 is located within the individual's 102 dwelling. For example, the individual 102 may install the smart vital device 108 within the individual's home. The smart vital device 108 may use the sensor information to determine the health condition, medical condition, and a degree of accuracy of the medical condition (e.g., whether the individual 102 is sick) and provide a notification of this to the individual 102. Accordingly, the individual 102 may use the smart vital device 108 as a monitoring device to determine whether/when the individual is sick. As such, the individual 102 might not go outside and interact of others, which may cause the spread of the affliction to be reduced/prevented.

Figure 4:
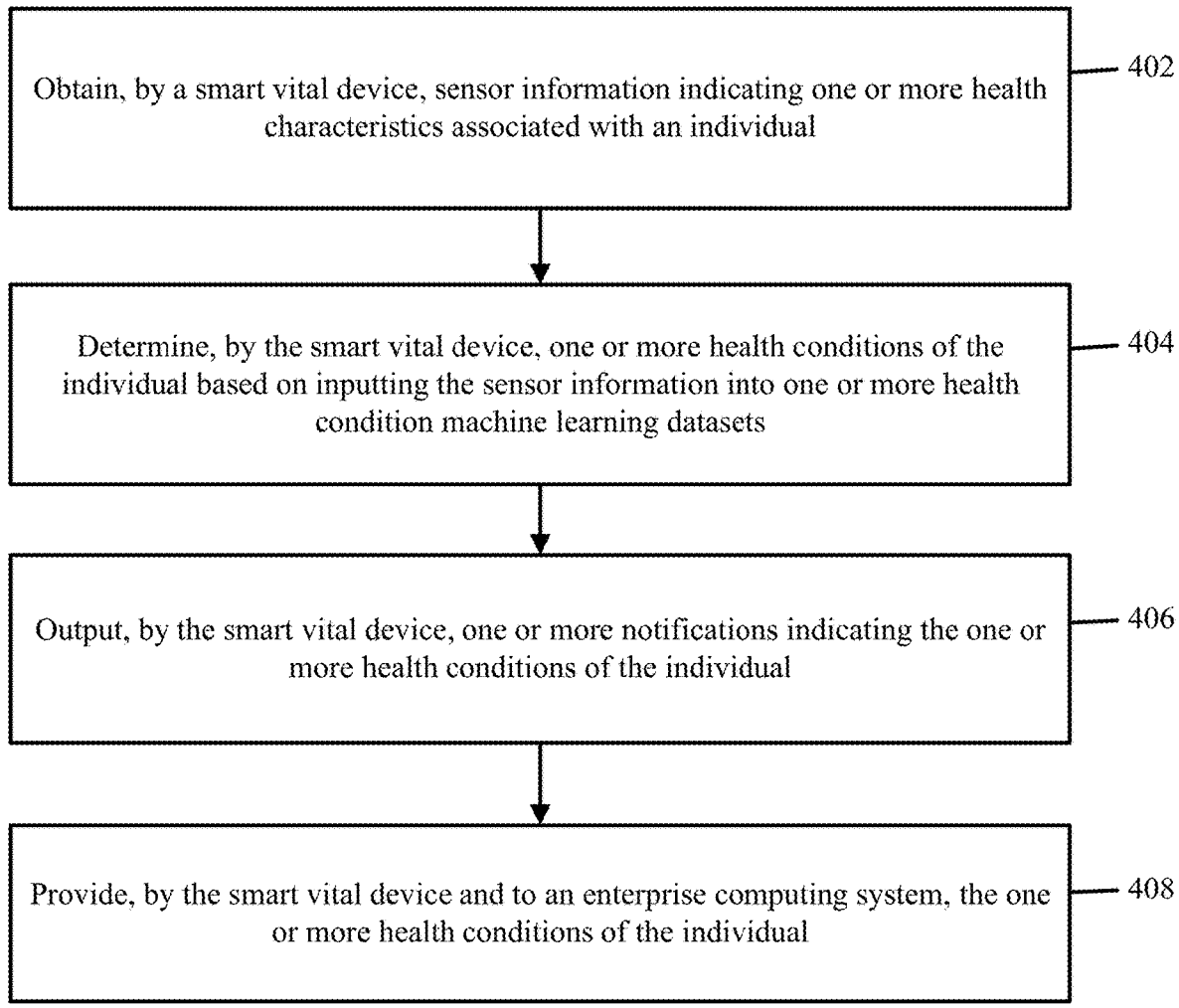
FIG. 4 is an exemplary process for operating a smart vital device to determine health conditions using artificial intelligence algorithms in accordance with one or more exemplary embodiments of the present application.

FIG. 4 is an exemplary process 400 for operating a smart vital device 108 to determine health conditions using artificial intelligence algorithms in accordance with one or more exemplary embodiments of the present application. The process 400 may be performed by the smart vital device 108 shown in FIG. 3; however, it will be recognized that a smart vital device 108 that includes additional and/or fewer components as shown in FIG. 3 may be used to perform process 400 and that any of the following blocks may be performed in any suitable order. The descriptions, illustrations, and processes of FIG. 4 are merely exemplary and the process 400 may use other descriptions, illustrations, and processes to determine health conditions.

At block 402, the smart vital device 108 obtains sensor information indicating one or more health characteristics associated with an individual such as individual 102. For example, referring to FIG. 3 and as described above, the smart vital device 108 may include one or more sensors such as the temperature sensor 306, the audio sensor 308, the humidity sensor, the visual sensor, and/or additional sensors. The sensors obtain sensor information of an area surrounding the smart vital device 108. The sensor information may indicate temperatures of the surrounding area, sounds/audio signals, water vapor content (e.g., humidity), and/or visual images of the individual 102.

In other words, the sensors (e.g., 306 and/or 308) may monitor an area surrounding the smart vital device 108 and feed sensor information to the smart vital processor 310. As the individual 102 comes within the proximity of the smart vital device 108, the sensors (e.g., sensor 306 and/or 308) may obtain sensor information associated with the individual 102.

At block 404, the smart vital device 108 determines one or more health conditions of the individual based on inputting the sensor information into one or more health condition machine learning datasets (e.g., machine learning datasets 314). For example, the smart vital processor 310 may retrieve the health condition machine learning datasets from the memory 312 and receive the sensor information from the one or more sensors. The smart vital processor 310 may input the sensor information into the retrieve health condition machine learning datasets to generate data indicating whether the individual 102 has one or more health conditions (e.g., symptoms).

In some instances, the sensor information indicates audio information (e.g., audio signals) from the audio sensor 308. For example, the audio sensor 308 obtains sounds, converts the sounds into audio files, and provides the audio files to the smart vital processor 310. The smart vital processor 310 inputs the audio files into the health condition machine learning datasets to generate data indicating whether the audio files indicate health conditions such as a sneeze, cough, and/or other types of sounds indicative of the individual 102 having symptoms of being sick.

In some examples, the sensor information indicates temperature information (e.g., an IR temperature image) from the temperature sensor 306. For example, the temperature sensor 306 captures IR images of the surrounding area and at least some of these images may include one or more individuals (e.g., individual 102). The temperature sensor 306 provides these images to the smart vital processor 310. The smart vital processor 310 determines whether the images include one or more individuals and/or whether the individuals have an elevated and/or abnormal temperature. For example, the IR image may be color-coded and based on a comparison of other images and/or a color code, the smart vital processor 310 may determine a numerical temperature value associated with portions of the IR image. Furthermore, either in parallel with determining the numerical temperature value and/or in series with the determination (e.g., before and/or after determining the numerical temperature value), the smart vital processor 310 may determine whether the image includes an individual. For example, people have general features that make them distinguishable from inanimate objects such as above a certain height or size. The smart vital processor 310 may determine, based on a height or size of a block within the image, whether the IR image includes the individual and if it includes an individual, a specific location within the image that the individual is situated. The smart vital processor 310 may use these determinations (e.g., the specific location within the IR image and the temperature value at the specific location) to determine whether the individual 102 has a fever or elevated temperature. For instance, the smart vital processor 310 may compare the temperature value of the individual 102 to temperature threshold to determine whether the individual has a fever.

In other words, the smart vital processor 310 uses the temperature readings (e.g., IR image) provided by the temperature sensor 306 to assess whether the temperature readings belong to an individual 102 and whether these readings indicate that the individual 102 has an elevated temperature.

Additionally, and/or alternatively, in some variations, the smart vital processor 310 may determine temperatures associated with particular body parts of the individual. For example, the smart vital processor 310 may determine a location of the head area or even the earlobe of the individual 102 within the image. The smart vital processor 310 may determine temperature readings at these locations and based on comparing them with a threshold, may further determine whether this information indicates the individual has an elevated temperature/fever.

Additionally, and/or alternatively, in some instances, the smart vital processor 310 may input the temperature information into the health condition machine learning datasets to generate data indicating whether individual 102 has one or more health conditions (e.g., fever). For example, by inputting the temperature information into the health condition machine learning datasets, the smart vital processor 310 may determine whether the image includes an individual 102, certain body parts of the individual, and/or temperature readings/values associated with the individual 102 and/or body parts of the individual 102 such as the earlobe. Additionally, and/or alternatively, the smart vital processor 310 may determine whether the image indicates the individual 102 has a fever.

In some instances, the sensor information indicates humidity/water vapor content information (e.g., moisture content) from the humidity sensor. For example, the humidity sensor obtains moisture content within the area surrounding the smart vital device 108. The smart vital processor 310 determines based on the moisture content whether the individual 102 has one more health conditions. For instance, the smart vital processor 310 may compare the received moisture content to one or more thresholds to determine whether the individual 102 has one or more health conditions such as a cold sweat. Additionally, and/or alternatively, in some examples, the smart vital processor 310 may input the humidity/water vapor content information into the health condition machine learning datasets to generate data indicating whether individual 102 has one or more health conditions (e.g., cold sweat). For example, by inputting the temperature information into the health condition machine learning datasets, the smart vital processor 310 may determine whether the moisture content indicates there is an individual 102 within the vicinity of the smart vital device 108 and whether the individual 102 has one or more health conditions.

In some examples, the sensor information indicates visual information (e.g., images and/or videos) from the visual sensor such as a camera, vision system, and so on. For example, the visual sensor obtains images and/or videos and provides these to the smart vital processor 310. The smart vital processor 310 inputs the visual information into the health condition machine learning datasets to determine whether an individual 102 is present and whether the individual 102 is showing health conditions. For instance, based on inputting the visual information into the health condition machine learning datasets, the smart vital processor 310 may indicate whether the individual 102 is showing health conditions such as if the individual 102 is sweating, limping, walking slowly, dizzy, feint, weak, eye dilation, skin discoloration, pimples, or other types of skin irritation.

After inputting the sensor information (e.g., visual information, humidity information, audio information, and/or temperature information) into the machine learning datasets, the smart vital processor 310 may generate data indicating whether the individual 102 has one or more health conditions. In some examples, the generated data may be in a Boolean format. For instance, for each health condition, the smart vital processor 310, using the machine learning datasets, indicates whether the individual 102 has the health condition (e.g., true or 1) or does not have the health condition (e.g., false or 0). For example, the generated data may indicate that the individual 102 has a fever based on the temperature information and/or a cough or sneeze based on the audio information.

Additionally, and/or alternatively, in some variations, the smart vital processor 310 determines a medical condition (e.g., whether the individual is sick) and/or a degree of accuracy of the medical condition based on the sensor information and/or the health conditions. For example, the smart vital processor 310 may input the sensor information into the one or more health condition machine learning datasets 314. Based on this, the smart vital processor 310 may generate health conditions as well medication conditions and/or a degree of accuracy associated with the medical condition. In other words, based on inputting the sensor information into the datasets 314, the smart vital processor 310 may determine the health conditions (e.g., symptoms of the individual 102 such as a fever and cough), the medical condition (e.g., the individual 102 is sick and/or a diagnosis of the affliction such as the individual 102 has the flu), and/or a degree of accuracy for the medical condition (e.g., there is a 96% chance the individual 102 is sick).

In some instances, the smart vital processor 310 determines medical conditions based on inputting health conditions into one or more machine learning datasets. For example, the smart vital processor 310 may determine the health conditions as described above (e.g., by inputting them into a machine learning dataset). The smart vital processor 310 may provide weights to each of the determined health conditions. Then, using one or more additional health condition machine learning datasets, the smart vital processor 310 may determine the medical condition for the individual 102 and/or a degree of accuracy for the medical condition. For instance, the smart vital processor 310 may input the determined health conditions and/or the weights associated with the health conditions into the additional health condition machine learning datasets to generate data indicating the medication condition and/or degree of accuracy for the individual 102.

At block 406, the smart vital device 108 outputs one or more notifications indicating the one or more health conditions of the individual 102. For example, referring to FIG. 3, the smart vital processor 310 may use an I/O device 316 to output a notification to the individual 102. In some instances, the notification may be an audio notification. For instance, the I/O device 316 may be an audio output device. The smart vital processor 310 may use a text-to-speech algorithm or some other method, process, and/or operation to output an audio indication associated with the determined health condition. For example, the audio indication may indicate the determined health condition (e.g., the individual 102 has a fever), the determined medical condition (e.g., the individual 102 is sick), and/or the degree of accuracy associated with the determined medical condition (e.g., 96% chance the individual 102 is sick).

In some examples, the notification may be a visual notification. For instance, the I/O device 316 may be a visual output device such as a display device/screen. The smart vital processor 310 may use the visual output device to output a visual indication associated with the determined health condition. For example, the visual indication may indicate the determined health condition (e.g., the individual 102 has a fever), the determined medical condition (e.g., the individual 102 is sick), and/or the degree of accuracy associated with the determined medical condition (e.g., 96% chance the individual 102 is sick).

In some variations, the notification may be a combination of a visual notification, an audio notification, and/or additional types of notifications such as a pop-up notification on the user device 104. For example, the smart vital device 108 may provide health information to the user device 104 either directly and/or via the enterprise computing system 110/the network 106. For instance, using a wireless connection such as BLUETOOTH connection or other type of short-range wireless connection, the smart vital device 108 may provide the information to the user device 104. Based on the information from the smart vital device 108, the user device 104 may display a notification on a display screen of the user device 104 (e.g., by using the software application installed on the user device 104 and associated with the enterprise organization). For example, the user device 104 may display a notification indicating the determined health condition, the determined medical condition, and/or the degree of accuracy associated with the determined medical condition. Additionally, and/or alternatively, the smart vital device 108 may provide this information to the enterprise computing system 110 via the network 106. The enterprise computing system 110 may then provide this information to the user device 104, which may cause the user device 104 to display the notification.

In some instances, the smart vital device 108 may output the one or more notifications to a computing device (e.g., network element) that is not associated with the individual 102. For instance, the smart vital device 108 may be located within a physical location that includes one or more other computing devices. In other words, a physical location such as a storefront may include the smart vital device 108 and additional devices (e.g., network element) such as employee devices used to perform additional functionalities (e.g., a pharmacy computing device used for providing prescriptions to individuals 102 and/or other computing devices within the storefront). The smart vital device 108 may use the network interface 318 to provide instructions indicating for the other computing device to display the one or more notifications (e.g., the determined health condition, the determined medical condition, and/or the degree of accuracy) to another computing device. In other words, in some examples, an employee that works at the storefront may be able to view the notifications on another computing device (e.g., at the pharmacy section of the storefront and/or at the check-out section of the storefront) and perform mitigation strategies based on the notification that the individual 102 is displaying symptoms and/or may be sick.

Figure 5:
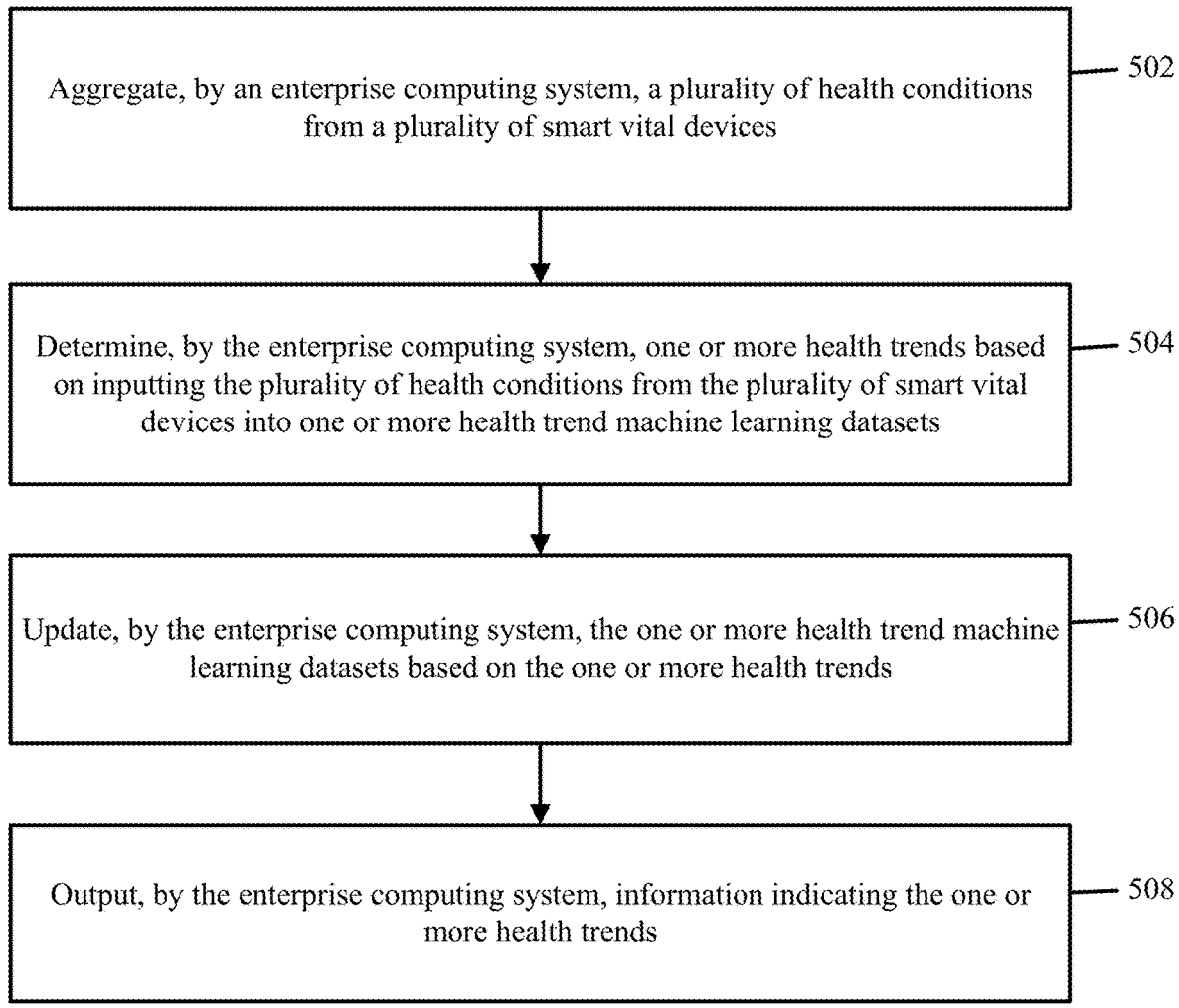
FIG. 5 is another exemplary process for operating an enterprise computing system using the determined health conditions in accordance with one or more exemplary embodiments of the present application.

At block 408, the smart vital device 108 provides the one or more health conditions of the individual 102 to an enterprise computing system 110. For example, using the network interface 318, the smart vital device 108 may provide the one or more determined health conditions, the one or more medical conditions, and/or the degree of accuracy associated with the one or more medical conditions to the enterprise computing system 110. FIG. 5 will describe the enterprise computing system 110 using the one or more determined health conditions, the one or more medical conditions, and/or the degree of accuracy in more detail.

FIG. 5 is another exemplary process 500 for operating the enterprise computing system 110 in accordance with one or more exemplary embodiments of the present application. The process 500 may be performed by the enterprise computing system 110 shown in FIG. 1; however, it will be recognized that any device, system, server and/or other computing apparatus may be used to perform process 500 and that any of the following blocks may be performed in any suitable order. The descriptions, illustrations, and processes of FIG. 5 are merely exemplary and the process 500 may use other descriptions, illustrations, and processes to determine trends based on health conditions.

At block 502, the enterprise computing system 110 aggregates a plurality of health conditions from a plurality of smart vital devices 108. For example, as mentioned above, there may be a plurality of smart vital devices 108 within a physical location (e.g., storefront) and/or across numerous geographical areas. After determining the health conditions of individuals such as individual 102, each of the smart vital devices 108 may provide the health conditions, medical conditions, and/or degree of accuracy to the enterprise computing system 110.

Additionally, and/or alternatively, the smart vital devices 108 may also provide further information associated with the health condition and/or the associated individual. For instance, the smart vital devices 108 may provide further information indicating a time/date associated with the determined health condition and/or a location associated with the determined health condition (e.g., identification of the physical storefront and/or a geographical area such as a city, state, locale, zip code, and/or latitude/longitude coordinates). The enterprise computing system 110 may aggregate the information from the smart vital devices 108 such as by classifying the information based on the date/time and/or the location. For instance, the enterprise computing system 110 may classify/group all health conditions for a given date/time window. Additionally, and/or alternatively, the enterprise computing system 110 may classify/group all health conditions for a given location (e.g., zip code or city).

At block 504, the enterprise computing system 110 determines one or more trends based on inputting the plurality of health conditions from the plurality of smart vital devices 108 into one or more health trend machine learning datasets. For example, the enterprise computing system 110 may input health conditions (e.g., coughs, sneezes, fevers, and so on) into the health trend machine learning datasets to perform regression analysis on the health conditions. For instance, using the health trend machine learning datasets and the health conditions from the smart vital devices 108, the enterprise computing system 110 may generate data indicating trends such as a time frame for when an affliction will peak (e.g., become most extreme) and/or when an affliction is likely going to end. In other words, by inputting the data from the devices 108 such as fevers, coughs, and so on, the enterprise computing system 110 may determine statistically significant data associated with an affliction (e.g., a disease such as a flu during a flu season). For instance, using the datasets and the health conditions, the enterprise computing system 110 may determine a projected peak of the affliction (e.g., peak number of cases during the flu season) and/or a projected end-date of the affliction (e.g., when the flu season is expected to end).

In some variations, the enterprise computing system 110 may use a classification/filter (e.g., time/date and/or location information) to generate the data indicating the trends. For example, the enterprise computing system 110 may classify the health conditions from the plurality of smart vital devices 108 based on the time/date associated with the health conditions (e.g., health conditions received between January $1^{st}$ through January $3^{nd}$ and/or health conditions received in the last few days such as last three days or last two weeks). The enterprise computing system 110 may input the health conditions matching these classifications into the health trend machine learning datasets to generate the data indicating the trends. In other words, in some instances, based on using the classifications (e.g., last two weeks of health trends), the enterprise computing system 110 may extrapolate the data out to determine the projected peaks and/or end-date.

Additionally, and/or alternatively, the enterprise computing system 110 may use the location information associated with the health conditions to generate the data indicating the trends. For example, the enterprise computing system 110 may classify the health conditions based on the location information (e.g., zip-code, city, state, geographical region/area). The enterprise computing system 110 may input the health conditions matching these classifications into the health trend machine learning datasets to generate the data indicating the trends. In other words, in some stances, based on using the classifications (e.g., city of Chicago), the enterprise computing system 110 may extrapolate the data out to determine the projected peaks and/or end-date for a particular location (e.g., Chicago).

Additionally, and/or alternatively, the enterprise computing system 110 may input the health conditions, date/time, and/or location information into the health trend machine learning dataset to generate the data indicating the trends. Additionally, and/or alternatively, the enterprise computing system 110 may first generate the data indicating the trends and then perform classification/filtering operation (e.g., classify/filter data generated from the machine learning datasets based on time/date and/or location information).

In some variations, instead of determining the medical conditions and/or degree of accuracy associated with the medical conditions at the smart vital device 108, the enterprise computing system 110 may determine the medical conditions and/or degree of accuracy associated with the medical conditions. For example, the enterprise computing system 110 may use the health conditions associated with the individual 102 and/or the data indicating the trends (e.g., peaks/end-date of the health conditions) to determine a medical condition (e.g., whether the individual 102 is sick) and/or a degree of accuracy of the medical condition.

Figure 6A:
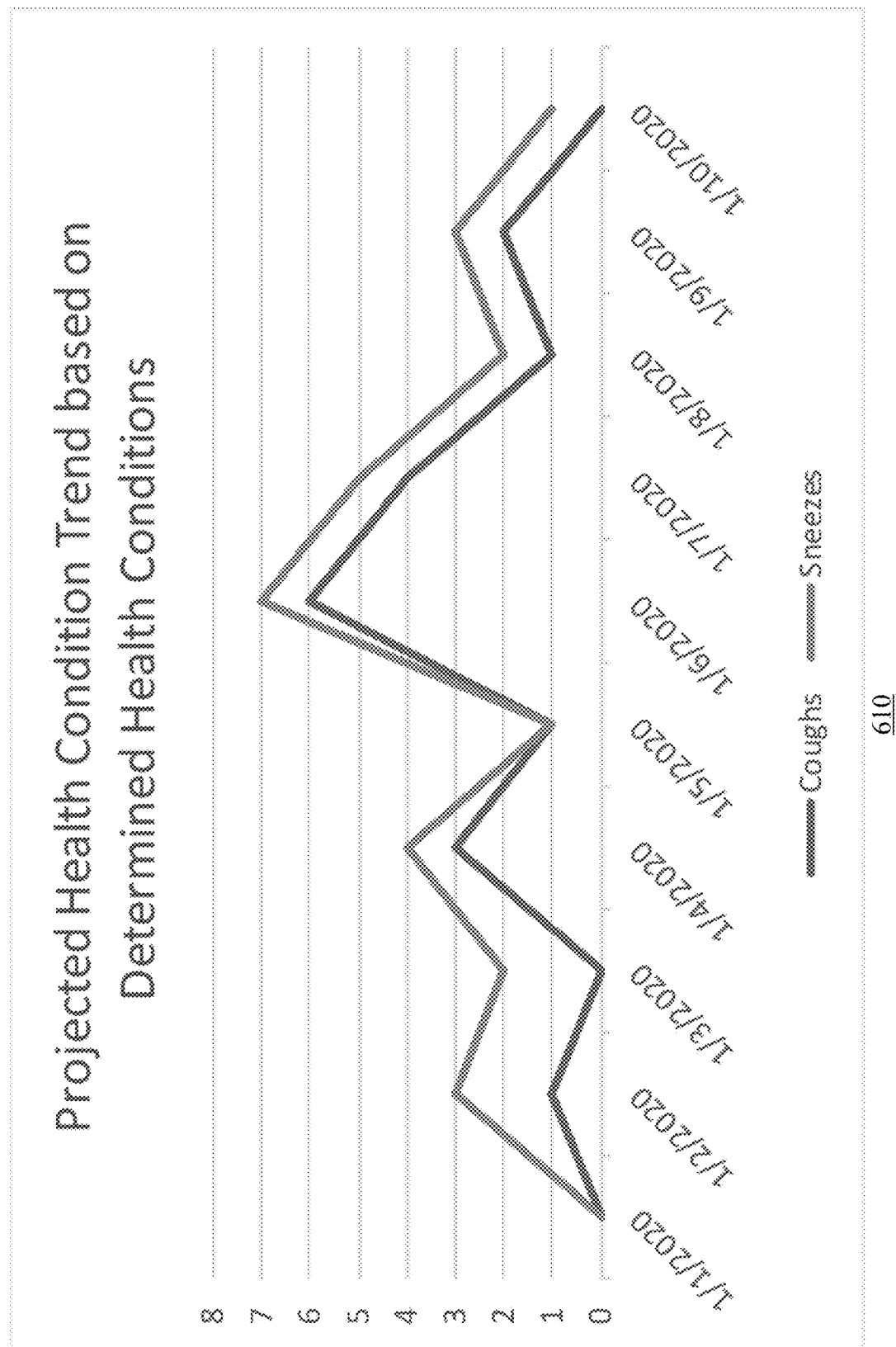
FIGS. 6a and 6b show health condition trends based on the determined health conditions from the smart vital device in accordance with one or more exemplary embodiments of the present application.
Figure 6B:
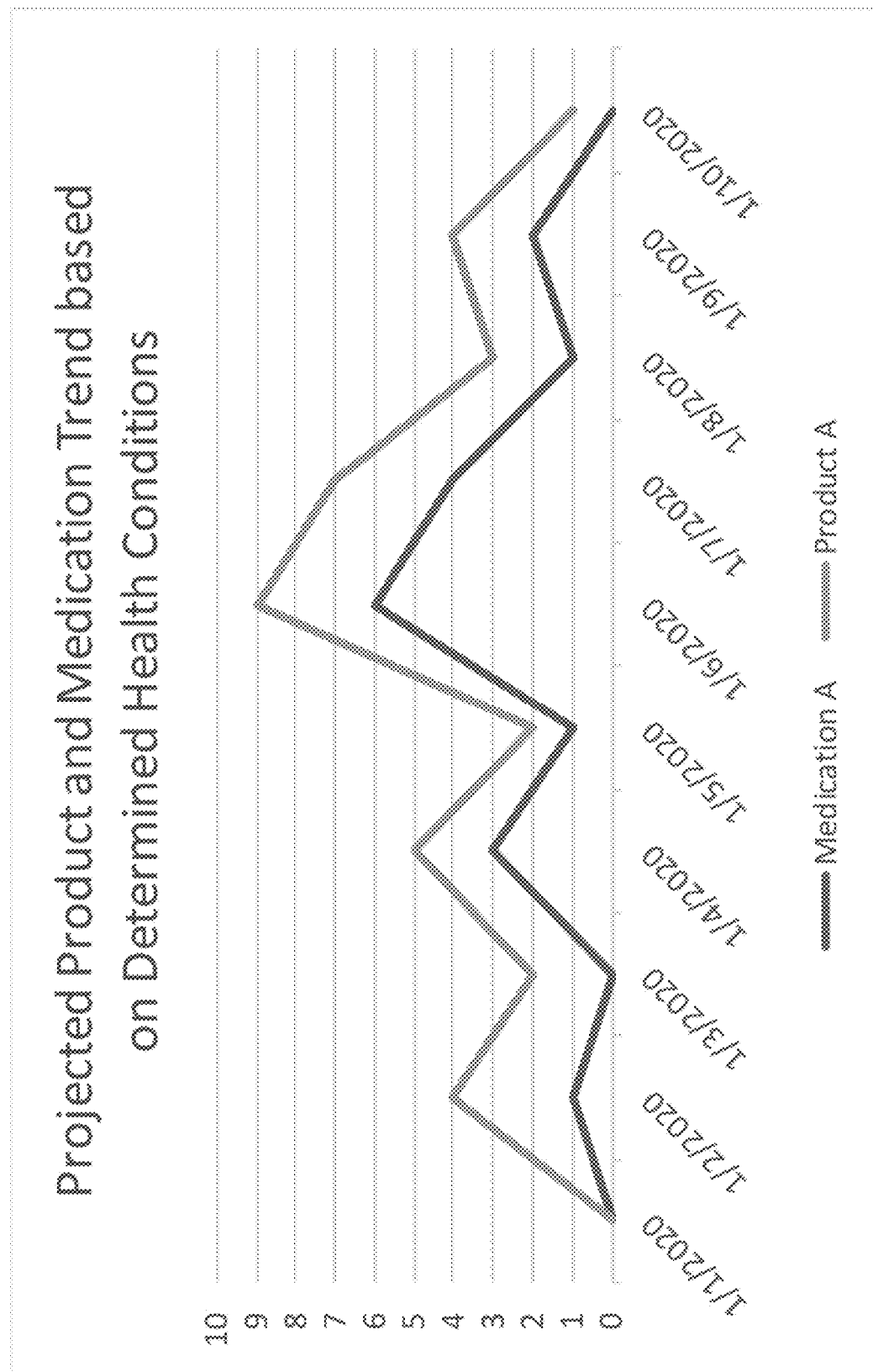

FIGS. 6a and 6b show exemplary health condition trends using the determined health conditions from the smart vital device 108 and will be used to describe block 504 in more detail. For instance, referring to FIG. 6a, the enterprise computing system 110 may classify/filter the health conditions based on a time/date such as between Jan. 1, 2020 to Jan. 3, 2020. Additionally, and/or alternatively, the enterprise computing system 110 may classify/filter the health conditions based on a location such as Chicago. Then, the enterprise computing system 110 may input these health condition entries (e.g., coughs, sneezes, fevers) into the health trend machine learning datasets to generate the projected health condition trend 610. As shown, the health condition trend 610 extrapolates the entries through Jan. 10, 2020. Using this trend 610, the enterprise computing system 110 may determine the peak of the affliction as Jan. 6, 2020 and the end of the affliction as Jan. 10, 2020.

Additionally, and/or alternatively, the trends may indicate medications (e.g., pharmaceutical drugs, tablets, pills, vitamins, and/or other types of medications able to be taken by an individual), products, and/or lines of products rather than the health conditions. For instance, referring to FIG. 6b and trend 620, each of the lines (e.g., coughs/sneezes) may indicate medications (e.g., medication A) and/or actual products (e.g., product A). For example, product A may include, but is not limited to, cough lozenges, suppressants, tea, honey, chloraseptic, and the like. Additionally, and/or alternatively, the trends may indicate entire product lines. The enterprise computing system 110 may determine trends such as when is the peak demand time for the product/lines of products/medications and/or an end demand time for the product/lines of product/medications.

At block 506, the enterprise computing system 110 updates the one or more health trend machine learning datasets based on the one or more trends. For example, the enterprise computing system 110 may update the health trend machine learning datasets using the data generated from block 504. As described above, the health trend machine learning datasets may be a supervised machine learning dataset, an unsupervised machine learning dataset, and/or a deep learning dataset. Further, this dataset may also be different from the health condition machine learning datasets 314. The enterprise computing system 110 may receive expected information such as an expected peak date of the affliction and/or an expected end-date of the affliction. Based on the expected information and the actual information, the enterprise computing system 110 may update the one or more health trend machine learning datasets. For instance, in some examples, referring to FIG. 6a, the expected peak date may be Jan. 9, 2020 and the actual peak date indicated in FIG. 6a is Jan. 6, 2020. Accordingly, the enterprise computing system 110 may update the health trend machine learning datasets based on the discrepancy.

In some examples, the one or more health trend machine learning datasets may be continuously trained and updated by the enterprise computing system 110. For example, the enterprise computing system 110 may initially train one or more health trend machine learning datasets using test data. Then, after each iteration or after a number of iterations of performing block 504, the enterprise computing system 110 may use actual data (instead of solely test data) to continuously train the health trend machine learning datasets. For the next iteration, the enterprise computing system 110 may use the updated health trend machine learning datasets to determine the data indicating the trends (e.g., new peaks/end-dates).

At block 508, the enterprise computing system 110 outputs information indicating the one or more health trends. For example, the information may indicate the projected peak of the affliction and/or the projected end-date of the affliction. Additionally, and/or alternatively, the enterprise computing system 110 may determine and provide one or more recommendations based on the health trends. For instance, the recommendation may indicate for the enterprise organization to obtain additional products (e.g., tissue paper, medications, groceries, and so on) based on the health trends. In other words, at the peak of the affliction (e.g., peak of flu season), individuals may purchase additional tissue paper or medication such as flu medication. The enterprise computing system 110 may provide information indicating the recommendations such as the enterprise organization should prepare for the peak of the affliction by stocking up on certain products earlier. Thus, the enterprise organization may be better prepared when the peak occurs. In some examples, the trends may indicate peak demand times/end times for products/product lines. Accordingly, the enterprise computing system 110 may provide information indicating the recommendations based on the product information. In some instances, the recommendation may indicate for employees of the enterprise organization to prepare for the event (e.g., the peak of the affliction).

Additionally, and/or alternatively, the enterprise computing system 110 may use location information associated with the health conditions to determine the health trends. As such, the recommendation may indicate and/or reflect the location information as well. For instance, the enterprise computing system 110 may indicate that Chicago area storefronts may experience a peak of the affliction in 2 weeks and as such, the recommendation may indicate for storefronts within the location (e.g., Chicago) to prepare by stocking up on certain products.

The output may be notification, alert, or flag for the enterprise organization. For instance, the enterprise computing system 110 may output a flag or display to another computing device indicating the health trends and/or the recommendations. The output may include instructions indicating for an employee to take action based on the health trends/recommendation (e.g., purchasing/stocking up on more product).

Figure 7:
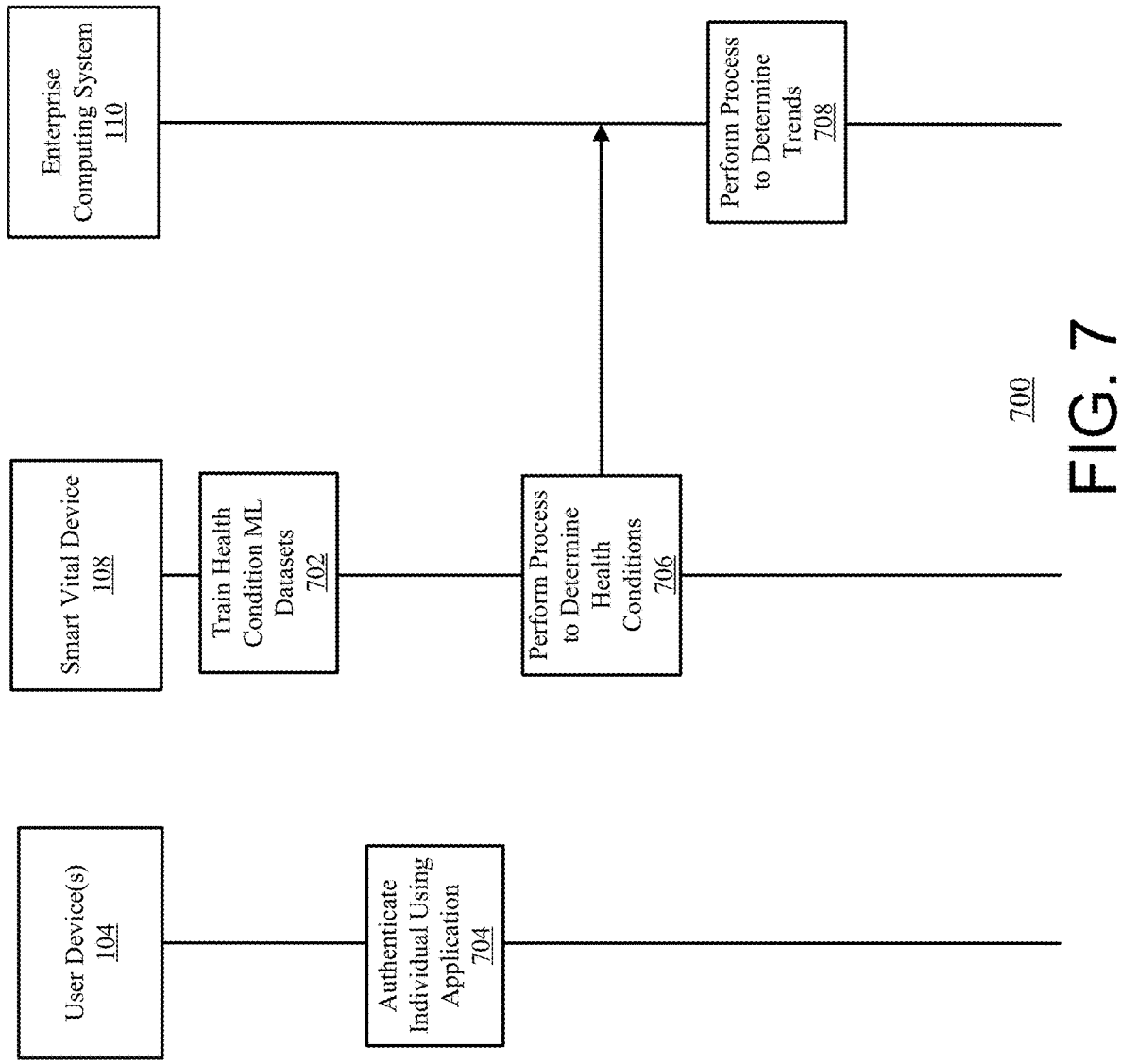
FIG. 7 is an exemplary event sequence for determining health conditions using machine learning algorithms in accordance with one or more exemplary embodiments of the present application.

FIG. 7 shows an exemplary event sequence 700 for determining and using health conditions and will be used to describe processes 400 and 500 in more detail. However, the event sequence 700 is merely an example and other types of event sequences are contemplated herein including by performing any of the following blocks in any suitable order.

At block 702, the smart vital device 108 may train the health condition machine learning datasets 314. For instance, referring to FIG. 3, the health condition machine learning datasets 314 may include one or more datasets. Each dataset may be associated with a health condition, multiple health conditions, a sensor, and/or multiple sensors. For instance, each health condition such as a fever may have an associated machine learning dataset. Additionally, and/or alternatively, multiple health conditions such as the cough and sneeze may have a singular associated machine learning dataset.

The smart vital device 108 may train the health condition machine learning datasets 314 by using expected/actual data. For instance, in some examples, for the machine learning dataset associated with the fever health condition, the smart vital device 108 may receive data indicating temperature ranges of individuals that are sick. The data of temperature ranges may indicate a range of numbers and/or may be color coded to indicate the temperatures of the individuals. The smart vital device 108 may train the health condition machine learning datasets based on inputting this data into the health condition machine learning dataset and comparing the output with the expected output. For example, the output from the health condition machine learning dataset may indicate the individual is not sick whereas the expected output would be the individual is sick. As such, the smart vital device 108 may update/train the health condition machine learning datasets accordingly until it reaches a certain accuracy threshold (e.g., 95%). After reaching the threshold, the smart vital device 108 may store the trained dataset in member.

In some instances, for the machine learning dataset associated with the audio information (e.g., coughs, sneezes, and so on), the smart vital device 108 may train these datasets similarly to the fever health condition. For instance, the smart vital device 108 may receive data indicating coughs, sneezes, and so on. The data may be audio data in a particular format and the smart vital device 108 may convert this audio data into another format prior to training the dataset (e.g., converting to a WAV format beforehand). Then, the smart vital device 108 may use this data similar to the temperature information to train the health condition machine learning dataset. For instance, the smart vital device 108 may classify the received data as a cough and the output from the ML dataset may indicate that it is not a cough. Accordingly, the smart vital device 108 may train the ML dataset accordingly based on the discrepancy. In other instances, the smart vital device 108 may train the datasets based on the sensors and/or other health conditions (e.g., based on a humidity/image indicating the individual is sweating and/or based on images of individuals limping, walking slowly, dizzy, feint, weak, skin discoloration, and so on).

In yet other instances the ML datasets may be associated with particular sensors. For example, the audio sensor may have one or more associated ML datasets. The smart vital device 108 may train these ML datasets for the sensors based on received data.

At block 704, the user device 104 may authenticate an individual (e.g., individual 102) using a mobile application. For example, the enterprise organization may own/operate/manage a mobile application with a sign-on for individuals. The individual 102 may authenticate themselves using the user device 104. Then, based on the authentication, the smart vital device 108 and/or the enterprise computing system 110 may associate health conditions with the individual 102. In some examples, the user device 104 may provide user authentication information (e.g., username, password, and other types of authentication information) to the enterprise computing system 110. The enterprise computing system 110 may authenticate the individual (e.g., individual 102) associated with the user device 104 based on the authentication information. Additionally, and/or alternatively, the user device 104 may authenticate the individual 102 based on the user device 104 being within a certain proximity of a smart vital device 108. For instance, as mentioned above, the user device 104 and the smart vital device 108 may communicate using the network interface 318 of the smart vital device 108. Based on the user device 104 and the smart vital device 108 being within a certain proximity (e.g., based on the smart vital device 108 comparing the signal from the user device 104 with a signal strength threshold), the user device 104 may provide user information associated with the individual 102. Using the user information, the smart vital device 108 may authenticate the individual 102.

At block 706, the smart vital device 108 may perform one or more operations/processes to determine the health conditions. For example, the smart vital device 108 may perform any or all blocks and descriptions described above from process 400. In some instances, for example, the smart vital device 108 may determine the health conditions based on sensor information and provide the health conditions to the enterprise computing system 110. Additionally, and/or alternatively, based on authenticating the individual 102 using the user information from the user device 104 at block 704, the smart vital device 108 may provide information indicating the health conditions, medical conditions, and/or degree of accuracy associated with the medical conditions to the user device 104. The user device 104 may display a notification indicating the health/medical conditions and/or the degree of accuracy. Additionally, and/or alternatively, the smart vital device 108 may determine one or more recommendations such as product recommendations and/or coupons based on the health conditions, medical conditions, and/or degree of accuracy and provide these recommendations to the user device 104. The user device 104 may display these recommendations.

At block 708, the enterprise computing system 110 may perform one or more operations/processes to determine the trends. For example, the enterprise computing system 110 may perform any or all blocks and descriptions described above from process 500. In some instances, for example, the enterprise computing system 110 may determine the trends based on health conditions and output the trends.

It will be appreciated that the figures of the present application and their corresponding descriptions are merely exemplary, and that the invention is not limited to these exemplary situations.

It will further be appreciated by those of skill in the art that the execution of the various machine-implemented processes and steps described herein may occur via the computerized execution of processor-executable instructions stored on a non-transitory computer-readable medium, e.g., random access memory (RAM), read-only memory (ROM), programmable read-only memory (PROM), volatile, nonvolatile, or other electronic memory mechanism. Thus, for example, the operations described herein as being performed by computing devices and/or components thereof may be carried out by according to processor-executable instructions and/or installed applications corresponding to software, firmware, and/or computer hardware.

The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the embodiments of the invention described herein are merely exemplary. Variations of these embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A system, comprising:
a first smart vital device, comprising:
one or more first processors; and
memory, wherein the memory stores one or more health condition machine learning models, and wherein the one or more first processors are configured to:
obtain sensor information indicating one or more health characteristics associated with an individual;
retrieve the one or more health condition machine learning models from the memory of the first smart vital device;
input the sensor information into the one or more health condition machine learning models to determine one or more health conditions of the individual;
output one or more notifications indicating the one or more health conditions of the individual; and
provide, to an enterprise computing system, the one or more health conditions of the individual; and
the enterprise computing system, wherein the enterprise computing system is configured to:
aggregate a plurality of health conditions from a plurality of smart vital devices, wherein the plurality of smart vital devices comprises the first smart vital device;
determine one or more health trends based on inputting the plurality of health conditions from the plurality of smart vital devices into one or more health trend machine learning models, wherein the one or more health trends indicate an expected time frame for an expected peak of an affliction;
receive actual information indicating an actual time frame for an actual peak of the affliction;
update the one or more health trend machine learning models based on the expected time frame and the actual time frame; and
output information indicating the one or more health trends.

2. The system of claim 1, wherein the first smart vital device comprises an audio sensor configured to provide audio information indicating audio signals from a surrounding environment and a temperature sensor configured to provide temperature information indicating temperature readings from the surrounding environment, and wherein obtaining the sensor information comprises obtaining the audio information and the temperature information.

3. The system of claim 2, the one or more first processors are further configured to:
determine, based on the temperature information, whether the temperature readings indicate a temperature of the individual,
wherein determining the one or more health conditions is further based on the temperature of the individual, and wherein the one or more health conditions indicate one or more symptoms of the individual.

4. The system of claim 2, wherein determining the one or more health conditions is based on inputting the audio signals into the one or more health condition machine learning models to generate the one or more health conditions, wherein the one or more health conditions indicate one or more symptoms of the individual.

5. The system of claim 2, wherein the first smart vital device further comprises a humidity sensor configured to provide humidity information indicating a humidity reading of the surrounding environment and an image sensor configured to capture an image of the individual, and wherein obtaining the sensor information comprises obtaining the humidity information and the captured image of the individual.

6. The system of claim 1, wherein the one or more first processors are further configured to:
receive, from a user device, user information indicating an identity of the individual, and
wherein outputting the one or more notifications indicating the one or more health conditions of the individual is based on the identity of the individual.

7. The system of claim 1, wherein the enterprise computing system is further configured to:

determine a network element associated with a location of the first smart vital device, and wherein outputting the information associated with the one or more health trends comprises outputting an alert to the network element associated with the location of the first smart vital device.

8. The system of claim 7, wherein the network element and the first smart vital device are located within a same geographical location and are separate devices.

9. The system of claim 1, wherein the one or more first processors are further configured to:

receive a plurality of audio files indicating coughs and/or sneezes;

receive a plurality of infrared images indicating elevated temperature readings of a plurality of individuals; and train the one or more health condition machine learning models based on the plurality of received audio files and the plurality of received infrared images.

10. The system of claim 1, wherein the one or more first processors are further configured to:

determine, based on the sensor information indicating the one or more health characteristics, a medical condition of the individual and a degree of accuracy associated with the medical condition, wherein the medical condition indicates whether the individual has the affliction.

11. The system of claim 10, wherein determining the medical condition of the individual and the degree of accuracy is based on inputting the sensor information and the one or more health conditions into the one or more health condition machine learning models.

12. The system of claim 1, further comprising a user device, wherein the one or more first processors are further configured to:

determine whether the user device is within a proximity of the first smart vital device; and provide the one or more health conditions of the individual to the user device based on determining the user device is within the proximity of the first smart vital device, and wherein the user device is configured to:

receive the one or more health conditions of the individual from the first smart vital device; and display a notification indicating the one or more health conditions of the individual.

13. The system of claim 1, wherein determining the one or more health trends comprises:

classifying, based on location information associated with the plurality of health conditions, the plurality of health conditions from the plurality of smart vital devices to determine classification information, wherein the location information indicates a particular geographic location; and determining the one or more health trends based on the one or more health trend machine learning models, the classification information, and the plurality of health conditions, wherein the one or more health trends further indicate the expected peak for the affliction at the particular geographic location.

14. A method, comprising:

receiving, by a smart vital device, sensor information indicating one or more health characteristics associated with an individual, wherein the sensor information comprises audio information indicating audio signals from a surrounding environment and temperature information indicating temperature readings from the surrounding environment;

determining, by the smart vital device, one or more health audio characteristics of the individual based on inputting the audio signals into one or more health condition machine learning models;

determining, by the smart vital device, one or more health temperature characteristics of the individual based on the temperature readings from the surrounding environment;

determining, by the smart vital device, a plurality of first health conditions of the individual based on the one or more health audio characteristics and the one or more health temperature characteristics;

based on the plurality of first health conditions and one or more weights associated with the plurality of health conditions, determining, by the smart vital device, a medical condition of the individual;

providing, by the smart vital device and to an enterprise computing system, the plurality of first health conditions and the medical condition of the individual;

determining, by the enterprise computing system, one or more health trends based on inputting a plurality of second health conditions from a plurality of smart vital devices into one or more health trend machine learning models, wherein the one or more health trends indicate an expected time frame for an expected peak of an affliction, and wherein the plurality of second health conditions comprise the plurality of first health conditions from the smart vital device;

receiving, by the enterprise computing system, actual information indicating an actual time frame for an actual peak of the affliction; and updating, by the enterprise computing system, the one or more health trend machine learning models based on the expected time frame and the actual time frame.

15. The method of claim 14, wherein the sensor information further comprises humidity information indicating a humidity reading of the surrounding environment, and wherein determining the plurality of first health conditions of the individual is further based on the humidity information.

16. The method of claim 14, wherein the sensor information further comprises a captured image of the individual, wherein the method further comprises:

determining, by the smart vital device, one or more image characteristics of the individual based on inputting the captured image into the one or more health condition machine learning models, and wherein determining the plurality of first health conditions is further based on the one or more image characteristics.

17. The method of claim 14, further comprising:

determining, by the smart vital device and based on the sensor information and the medical condition, a degree of accuracy associated with the medical condition; and outputting, by the smart vital device, the degree of accuracy.

18. The method of claim 14, wherein determining the medical condition of the individual further comprises:

inputting the plurality of first health conditions and the one or more weights associated with the plurality of first health conditions into one or more second machine learning models to determine the medical condition of the individual.

19. The method of claim 14, wherein each of the plurality of first health conditions is in a Boolean format, and wherein each of the plurality of first health conditions is associated with a weight from the one or more weights.

20. A non-transitory computer-readable medium having processor-executable instructions stored thereon, wherein the processor-executable instructions, when executed, facilitate:

receiving sensor information indicating one or more health characteristics associated with an individual, wherein the sensor information comprises audio information indicating audio signals from a surrounding environment and temperature information indicating temperature readings from the surrounding environment;

determining one or more health audio characteristics of the individual based on inputting the audio signals into one or more health condition machine learning models;

determining one or more health temperature characteristics of the individual based on the temperature readings from the surrounding environment;

determining a plurality of first health conditions of the individual based on the one or more health audio characteristics and the one or more health temperature characteristics;

based on the plurality of first health conditions and one or more weights associated with the plurality of first health conditions, determining a medical condition of the individual; and providing, to an enterprise computing system, the plurality of first health conditions and the medical condition of the individual, wherein the enterprise computing system determines one or more health trends based on inputting a plurality of second health conditions from a plurality of smart vital devices into one or more health trend machine learning models, wherein the one or more health trends indicate an expected time frame for an expected peak of an affliction, wherein the plurality of second health conditions comprise the plurality of first health conditions, and wherein the enterprise computing system receives actual information indicating an actual time frame for an actual peak of the affliction and updates the one or more health trend machine learning models based on the expected time frame and the actual time frame.

* * * * *